United States Patent [19]

Hamilton et al.

[11] 4,388,308

[45] Jun. 14, 1983

[54] N6-[(2-HYDROXYPROPYL)ARYL]ADENO-SINES

[75] Inventors: Robert W. Hamilton, Wilmette; Richard E. L. Henderson, Evanston; Barnett S. Pitzele, Skokie, all of Ill.

[73] Assignee: G.D. Searle & Co., Skokie, Ill.

[21] Appl. No.: 157,693

[22] Filed: Jun. 9, 1980

[51] Int. Cl.$^3$ .................... A61K 31/70; C07H 19/16
[52] U.S. Cl. .................................. 424/180; 536/26; 536/24
[58] Field of Search .................... 544/277; 536/26; 424/180

[56] References Cited

U.S. PATENT DOCUMENTS

| | | | |
|---|---|---|---|
| 3,929,763 | 12/1975 | Fauland et al. | 536/26 |
| 4,138,562 | 2/1979 | Vince | 544/277 |
| 4,221,910 | 9/1980 | Sorolla | 544/265 |
| 4,309,419 | 1/1982 | Wolberg et al. | 424/180 |
| 4,315,000 | 2/1982 | Cook | 424/180 |
| 4,340,730 | 7/1982 | Henderson et al. | 536/20 |

Primary Examiner—Nicholas S. Rizzo
Attorney, Agent, or Firm—W. Dennis Drehkoff; Albert Tockman

[57] ABSTRACT

N$^6$-2-hydroxypropylaryl-substituted adenosines and adenines represented by the formula

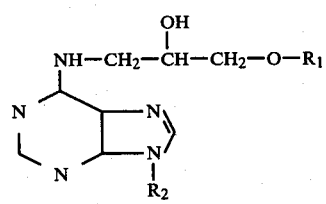

wherein R$_1$ is selected from the group consisting of naphthyl, phenyl, substituted phenyl or biphenyl; and R$_2$ is hydrogen or 1-$\beta$-ribosyl; and the pharmaceutically acceptable salts thereof. The compounds are anti-hypertensive agents.

15 Claims, No Drawings

$N^6$-[(2-HYDROXYPROPYL)ARYL]ADENOSINES

BACKGROUND OF THE INVENTION

Since the etiology of most cases of hypertension is unknown, the search for effective antihypertensive agents is largely empirical, and various classes of agents are currently employed for general antihypertensive therapy.

While a number of effective agents exist, because of the significant, adverse side-effects produced by all effective antihypertensive agents, and because of the frequent need to periodically change agents, the search for additional agents continues.

Various derivatives of adenosine and adenine have been reported to exhibit various pharmaceutical activities, i.e., antiviral activity, blood cholesterol lowering activity and cardiovascular activities. In the cardiovascular field, the adenosine derivatives have variously been reported to be useful as coronary dilators useful for treating angina pectoris, coronary insufficiency and myocardial infarct, and as blood platelet aggregate inhibitors.

$N^6$-substitution has been reported to produce adenosine derivatives which are useful as antihypertensive agents. See for example CA82:32 C(1957); CA83:71866m(1975); CA82:17136 (1975). $N^6$-substitution has also produced agents which exhibit widely varying activities, i.e., coronary dilating and blood platelet aggregration inhibitory activities (CA81:78193g(1974)); antipolytic and antihypercholesteremic activity (CA84:150915a(1976)); anti-tumor activity (Current Abstracts of Chemistry, 58, issue 605, 231440(1975); growth promoting activity (CA76:55126v(1972).

$N^6$-adenosine derivatives have been reported to act on the heart and blood circulation, especially on coronary circulation (NE68,12083) and $N^6$-$\beta$-naphthyl and aralkyl, phenyl and benzyl-substituted adenosines have been reported to exhibit coronary dilating and blood platelet aggregation-inhibiting activities.

The present invention provides $N^6$-(2-hydroxypropyl)aryl-substituted adenosines and adenines which are potent antihypertensive agents. This activity is wholly surprising because of the widely varying utilities of $N^6$-substituted adenosines and adenines.

SUMMARY

The present invention provides $N^6$-[(2-hydroxypropyl)aryl]adenosines and adenines which are useful as antihypertensive agents.

DETAILED DESCRIPTION OF PREFERRED EMBODIMENTS

The $N^6$-substituted adenosines and adenines of the present invention are represented by Formula I:

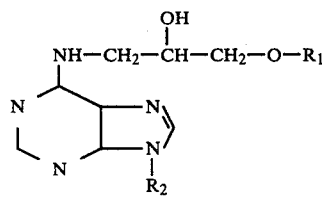

wherein $R_1$ is selected from the group consisting of naphthyl, phenyl, substituted phenyl or biphenyl and; $R_2$ is hydrogen or 1-$\beta$-ribosyl; and the pharmaceutically acceptable salts thereof.

When $R_2$ is hydrogen, the compounds of this invention are $N^6$-substituted adenines represented by Formula II:

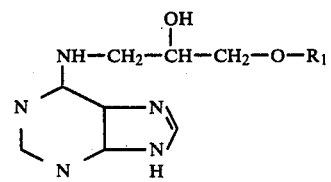

wherein $R_1$ is as defined in Formula I.

When $R_2$ is 1-$\beta$-ribosyl, the compounds of this invention are $N^6$-substituted adenosines represented by Formula III:

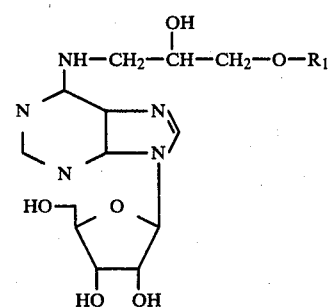

wherein $R_1$ is as defined in Formula I.

The compounds of this invention are useful as antihypertensive agents when administered orally to hypertensive mammalian patients in doses of 1.5 to 150 mg/kg daily, preferably from 15 to 50 mg/kg daily.

The preferred compound of formula I is $N^6$-[2-hydroxy-3-(1-naphthalenyloxy)propyl]adenosine.

Other preferred compounds include $N^6$-[2-hydroxy-3-(1-naphthalenyloxy)propyl]-9H-purin-6-amine; $N^6$-[3-(4-acetylphenoxy)-2-hydroxypropyl]adenosine; $N^6$-[3-(3-acetylphenoxy)-2-hydroxypropyl]adenosine; $N^6$-{3-([1,1'-biphenyl]-2-yloxy)-2-hydroxypropyl}adenosine; and $N^6$-{2-hydroxy-3-[(2-propenyl)phenoxy]propyl}adenosine.

The antihypertensive activity of the compounds of this invention was first determined in the spontaneously hypertensive rat. An initial intragastric dose of 50 mg/kg was administered to male, 11–16 week old spontaneously hypertensive rats, obtained from Laboratory Animal Supply Co., Indianapolis, Indiana, 46241, after maintaining them for at least 1 week in-house before use. Initial blood pressure was measured by a caudal plethysmograph immediately before administration of test compound. Blood pressure readings were repeated 4 and 24 hours after administration of the test compound. Dosages of 15 mg/kg (oral) of the preferred compound have been found to significantly lower blood pressure in this assay.

The following examples further illustrate the present invention.

EXAMPLE 1

Preparation of
$N^6$-[2-hydroxy-3-(1-naphthalenyloxy)propyl]adenosine 5.0 g (0.0174 moles) of 6-chloropurine riboside, 3.79 g (0.0174 moles) of (1-naphthalenyloxy)2-hydroxypropylamine, 3.52 g (0.0348 moles) of triethylamine and 100 ml of anhydrous ethanol were heated at reflux for 16 hours. Solvent was distilled off under vacuum. The resulting residue was partitioned between methylene chloride and water. The organic layer was separated, dried over $K_2CO_3$ and concentrated under vacuum. This residue was crystallized from ethanol or methanol. The solvated resultant product was dried under high vacuum, heating at a temperature just under its melting point, and raising that temperature as the melting point raised until all of the solvate was gone.

EXAMPLE 2

Preparation of
$N^6$-[2-hydroxy-3-(1-naphthalenyloxy)propyl]-9H-purin-6-amine

By substituting 6-chloropurine (2.69 g, 0.0174 moles) for the 6-chloropurine riboside in Example 1, $N^6$-[2-hydroxy-3-(1-naphthalenyloxy)propyl]-9H-purin-6-amine was obtained.

EXAMPLE 3

Preparation of
$N^6$-[3-(4-acetylphenoxy)-2-hydroxypropyl]-adenosine

By substituting (4-acetylphenoxy)-2-hydroxypropylamine (3.65 g, 0.017 mole) for the 2-hydroxy-(1-naphthalenyloxy)propylamine of Example 1 and following the method of Example 1, $N^6$-[3-(4-acetylphenoxy)-2-hydroxypropyl]-adenosine was obtained.

EXAMPLE 4

Preparation of
$N^6$-[3-(3-acetylphenoxy)-2-hydroxypropyl]adenosine

By substituting 2-hydroxy-3-acetylphenoxypropylamine (3.65 g, 0.017 mole) for the 2-hydroxy-1-naphthalenyloxypropylamine of Example 1, $N^6$-[3-(3-acetylphenoxy)-2-hydroxypropyl]adenosine was obtained.

EXAMPLE 5

Preparation of
$N^6$-{3-[(1,1'-biphenyl)-2-yloxy]-2-hydroxypropyl}-adenosine

By substituting (1,1'-biphenyl-2-yloxy)-2-hydroxypropylamine for the starting material in Example 1, $N^6$-{3-[(1,1'-biphenyl)-2-yloxy]-2-hydroxypropyl}-adenosine was obtained.

EXAMPLE 6

Preparation of
$N^6$-{2-hydroxy-3-[(2-propenyl)phenoxy]-propyl}-adenosine

By substituting 2-hydroxy-3-(propenylphenoxy)-propylamine (3.61 g, 0.0174 moles) for the starting material of Example 1, $N^6$-{2-hydroxy-3-[(2-propenyl)phenoxy]propyl}adenosine was obtained.

EXAMPLE 7

Preparation of
$N^6$-[3-(4-acetylphenoxy)-2-hydroxypropyl]-9H-purin-6-amine

By substituting 3-(4-acetylphenoxy)-2-hydroxypropylamine (3.65 g, 0.0174 moles) for the starting material of Example 2 and following the method of Example 2, the desired compound is obtained.

EXAMPLE 8

Preparation of
$N^6$-[3-(3-acetylphenoxy)-2-hydroxypropyl]-9H-purin-6-amine

By substituting 3-(3-acetylphenoxy)-2-hydroxypropylamine (3.65 g, 0.0174 moles) for the starting material of Example 2 and following the method of Example 2, the desired compound is obtained.

EXAMPLE 9

Preparation of
$N^6$-{3-[(1,1'-biphenyl)-2-yloxy]-2-hydroxypropyl}-9H-purin-6-amine By substituting 3-[(1,1'-biphenyl)-2-yloxy]-2-hydroxypropylamine (4.88 g, 0.0174 moles) for the starting material of Example 2 and following the method of Example 2, the desired compound is obtained.

EXAMPLE 10

Preparation of
$N^6$-{2-hydroxy-3-[(2-propenyl)phenoxy]-propyl}-9H-purin-6-amine By substituting 2-hydroxy-3-(2-propenylphenoxy)-propylamine (3.61 g, 0.0174 moles) for the starting material of Example 2 and following the method of Example 2, the desired compound is obtained.

EXAMPLE 11

Preparation of $N^6$-3-(4-acetylamidophenoxy)-2-hydroxypropyladenosine

By substituting 4-acetylamidophenoxy-2-hydroxypropylamine (3.90 g, 0.0174 moles) for the starting material in Example 2 and following the method of Example 2, the desired compound is obtained.

EXAMPLE 12

Preparation of
$N^6$-3-(4-acetylamidophenoxy)-2-hydroxypropyladenosine

By substituting 3-(4-acetylamidophenoxy)-2-hydroxypropylamine (3.90 g, 0.0174 moles) for the starting material of Example 2 and following the method of Example 2, the desired compound is obtained.

The compounds of this invention are administered orally and are formulated into suitable dosage forms for oral administration.

Solid dosage forms for oral administration include capsules, tablets, pills, powders and granules. In such solid dosage forms, the active compound is admixed with at least one inert diluent such as sucrose, lactose, or starch. Such dosage forms can also comprise, as is normal practice, additional substances other than inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspension, syrups, and elixirs containing inert diluents commonly used in the art, such as water. Besides inert diluents, such compositions can also include adjuvants, such as wetting agents, emulsifying and suspending agents, and sweetening, flavoring, and perfuming agents.

We claim:

1. An $N^6$-substituted adenosine represented by the formula:

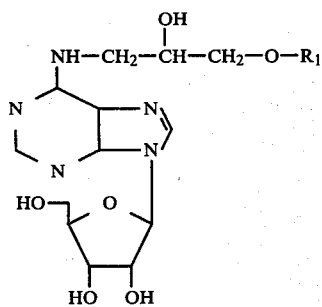

wherein $R_1$ is selected from the group consisting of naphthyl, acetylphenyl, 2-propenylphenyl and 1, 2-biphenyl; or a pharmaceutically acceptable salt thereof.

2. A pharmaceutical composition which is useful in treating a hypertensive patient composing an effective amount of a compound of claim 1 and a pharmaceutically acceptable carrier or diluent.

3. A pharmaceutical composition of claim 1, which is useful in treating a hypertensive patient suitable for oral administration.

4. A method of reducing blood pressure in a hypertensive mammalian patient comprising administering a therapeutically effective dose of a compound of claim 1 to said patient.

5. The method of claim 4 wherein said compound is administered orally.

6. A compound of claim 1: $N^6$-{2-hydroxy-3-[(2-propenyl)phenoxy]propyl} adenosine.

7. A compound of claim 1: $N^6$-[3-(3-acetylphenoxy)-2-hydroxypropyl] adenosine.

8. A compound of claim 1: $N^6$-[3-(4-acetylphenoxy)-2-hydroxypropyl] adenosine.

9. A compound of claim 1: $N^6$-[2-hydroxy-3-(1-Naphthalenyloxy)propyl] adenosine.

10. A compound of claim 1: $N^6$-{3-[1,1'-biphenyl)-2-yloxy]-2-hydroxypropyl} adenosine.

11. A pharmaceutical composition of claim 2, which is useful in treating a hypertensive patient, wherein said compound is: $N^6$-{2-hydroxy-3-[(2-propenyl)phenoxy]propyl}adenosine.

12. A pharmaceutical composition of claim 2, which is useful in treating a hypertensive patient, wherein said compound is: $N^6$-[3-(3-acetylphenoxy-2-hydroxypropyl] adenosine.

13. A pharmaceutical composition of claim 2, which is useful in treating a hypertensive patient, wherein said compound is: $N^6$-[3-(4-acetylphenoxy)-2-hydroxypropyl] adenosine.

14. A pharmaceutical composition of claim 2 which is useful in treating a hypertensive patient, wherein said compound is: $N^6$-[2-hydroxy-3-(1-naphthalenyloxy)propyl] adenosine.

15. A pharmaceutical composition of claim 2, which is useful in treating a hypertensive patient, wherein said compound is: $N^6$-{3-[(1,1'-biphenyl)-2-yloxy]-2-hydroxypropyl} adenosine.

* * * * *

UNITED STATES PATENT AND TRADEMARK OFFICE
CERTIFICATE OF CORRECTION

PATENT NO. : 4,388,308
DATED : June 14, 1983
INVENTOR(S) : Hamilton, et al

It is certified that error appears in the above-identified patent and that said Letters Patent are hereby corrected as shown below:

In the abstract, the correct structure is:

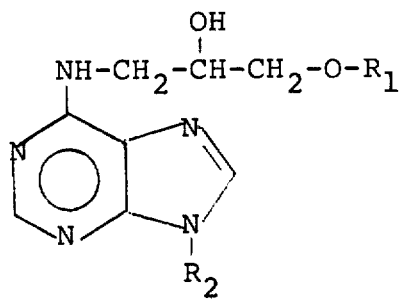

The correct Structure I in column 1 is:

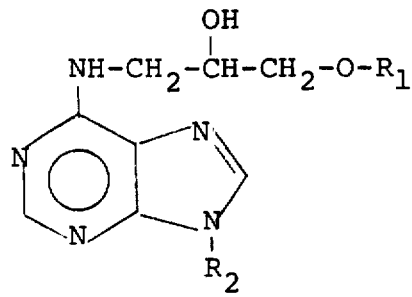

UNITED STATES PATENT AND TRADEMARK OFFICE
CERTIFICATE OF CORRECTION

PATENT NO. : 4,388,308

DATED : June 14, 1983

INVENTOR(S) : Hamilton, et al

Page 2 of 3

It is certified that error appears in the above-identified patent and that said Letters Patent are hereby corrected as shown below:

The correct Structure II in column 2 is:

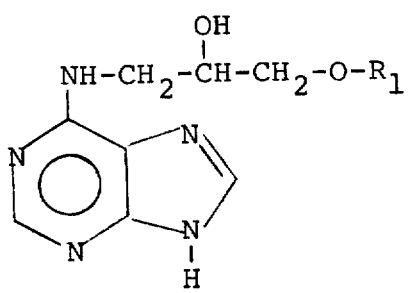

The correct Structure III in column 2 is:

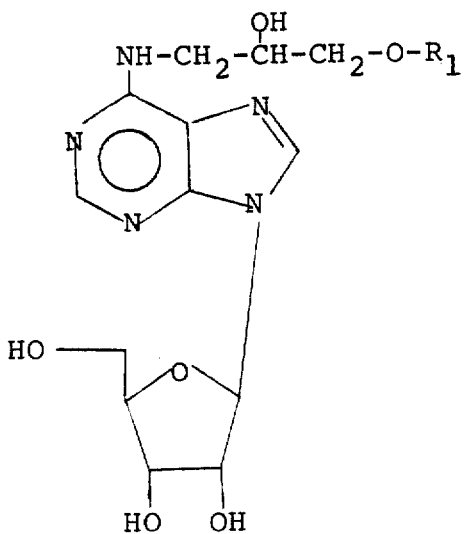

UNITED STATES PATENT AND TRADEMARK OFFICE
CERTIFICATE OF CORRECTION

PATENT NO. : 4,388,308
DATED : June 14, 1983
INVENTOR(S) : Robert W. Hamilton, Richard E.L. Henderson and Barnett S. Pitzele It is certified that error appears in the above-identified patent and that said Letters Patent are hereby corrected as shown below:

The correct Structure in Claim 1 is:

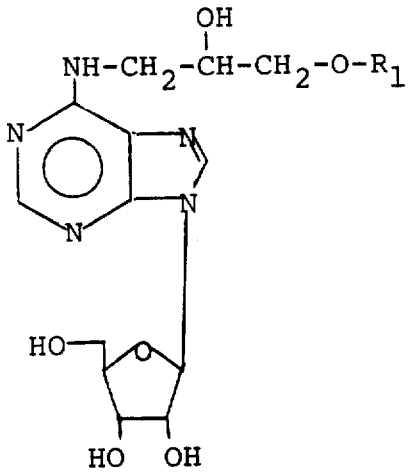

Signed and Sealed this

First Day of November 1983

[SEAL]

Attest:

GERALD J. MOSSINGHOFF

Attesting Officer     Commissioner of Patents and Trademarks